United States Patent
He et al.

(10) Patent No.: US 9,204,832 B1
(45) Date of Patent: Dec. 8, 2015

(54) TEST DEVICE AND ROTATION MODULE THEREOF

(71) Applicant: Lite-On Technology Corporation, Taipei (TW)

(72) Inventors: Sz-Shian He, Taipei (TW); Chia-Chun Wei, Taipei (TW); Hung-Wei Chen, Taipei (TW); Wei-Chieh Hu, Taipei (TW)

(73) Assignee: Lite-On Technology Corporation, Taipei (TW)

( * ) Notice: Subject to any disclaimer, the term of this patent is extended or adjusted under 35 U.S.C. 154(b) by 0 days.

(21) Appl. No.: 14/490,687

(22) Filed: Sep. 19, 2014

(30) Foreign Application Priority Data

May 26, 2014 (CN) .......................... 2014 1 0224741

(51) Int. Cl.
| | |
|---|---|
| *G01D 11/24* | (2006.01) |
| *A61B 5/151* | (2006.01) |
| *F16H 25/12* | (2006.01) |
| *A61B 5/15* | (2006.01) |

(52) U.S. Cl.
CPC ....... *A61B 5/15148* (2013.01); *A61B 5/150343* (2013.01); *A61B 5/150358* (2013.01); *F16H 25/125* (2013.01); *G01D 11/24* (2013.01)

(58) Field of Classification Search
CPC ...................................................... G01D 11/24
USPC ............................................................ 73/431
See application file for complete search history.

(56) References Cited

U.S. PATENT DOCUMENTS 7,190,465 B2 * 3/2007 Froehlich ............. G01C 15/002
356/601

* cited by examiner

*Primary Examiner* — Lisa Caputo
*Assistant Examiner* — Jamel Williams
(74) *Attorney, Agent, or Firm* — Jianq Chyun IP Office

(57) ABSTRACT

A test device and a rotation module thereof are provided. The rotation module includes a rotation body and a sleeve. The rotation body includes a shaft, a first tube element, and a second tube element. The shaft is pivoted in the housing, and has an annular protrusion. The first tube element and the second tube element are sleeved on the shaft respectively, and the second tube element is located between the first tube element and the annular protrusion. The sleeve is slidably disposed on the rotation body. When the sleeve moves between a first position and a second position back and forth, the second tube element is driven to rotate back and forth relative to the first tube element. The annular protrusion is respectively driven by second tube element and the sleeve drive the annular protrusion so that the shaft rotates relative to the first tube element.

15 Claims, 5 Drawing Sheets

TEST DEVICE AND ROTATION MODULE THEREOF

CROSS-REFERENCE TO RELATED APPLICATION

This application claims the priority benefit of China application serial no. 201410224741.8, filed on May 26, 2014. The entirety of the above-mentioned patent application is hereby incorporated by reference herein and made a part of this specification.

BACKGROUND OF THE INVENTION

1. Field of the Invention

The invention generally relates to a test device, and more particularly to a test device having a rotation module.

2. Description of Related Art

With development in technology and awareness in health issue, people pay more attentions each day to agendas such as health hygiene. Therefore, medical equipments have been constantly developed and improved in order to meet manufacturing standards of medical equipments as well as public demand.

Take a blood testing device as an example, in which many types of different blood-collecting devices have been derived, such as blood-collecting pen, lancets, blood-collecting tube and so on, so as to facilitate in simple blood testing. A test device is generally used together with single-use consumables. For example, the blood testing device on the market usually requires use of lancets and test sheets in bulk packing. Therein, the lancets and the test sheets belong to the single-use consumables which need to be thrown away once being used. According to current design of the test device, a user must manually install and remove the single-use consumables. For example, during the process in use, the user must manually install the lancets and the test sheets into the blood-collecting device. After a blood sample is obtained for testing, the user must again manually remove and throw away the lancets and the test sheets being used, and re-install the new lancets and the new test sheets the next time.

By doing so, although misgivings for bacterial infection or cross infection due to the consumables being repeatedly used by the user may be avoided, installing steps for the lancets and the test sheets are quite complicated to cause inconvenience for the user in use. Accordingly, it has became one of may important problems to be solved as how to improve the test device so it is able to automatically replace the consumables (e.g., the lancets and the test sheets) in the test device thereby improving convenience for the user in use.

SUMMARY OF THE INVENTION

The invention provides a test device having a rotation module, in which a carrying cartridge is driven by a unidirectional rotation characteristic of the rotation module to accomplish a purpose of automatically changing consumables installed in the carrying cartridge, so as to facilitate in improving convenience for the user in use.

A rotation module in the invention may be disposed in a housing of a test device. The rotation module includes a rotation body and a sleeve. The rotation body includes a shaft, a first tube element, and a second tube element. The shaft is pivoted in the housing, and the shaft has an annular protrusion. The first tube element is fixedly disposed in the housing and sleeved on the shaft, wherein the shaft is adapted to rotate relative to the first tube element. The second tube element is rotatably sleeved on the shaft and located between the first tube element and the annular protrusion. The sleeve is slidably disposed on the rotation body. When the sleeve moves from a first position to a second position, the second tube element is propelled by the annular protrusion to rotate a first angle along a rotating direction relative to the first tube element. When the sleeve moves from the second position to the first position, the second tube element is propelled by the sleeve to rotate the first angle along an opposite direction of the rotating direction relative to the first tube element, and the annular protrusion is respectively driven by the second tube element and the sleeve so that the shaft rotates a second angle relative to the first tube element.

A test device in the invention includes a housing, a carrying module, a driving gear module, a rotation body, and a push rod. The carrying module is pivoted on the housing, wherein the carrying module has a plurality of slots. The rotation module is disposed in the housing, and the rotation module includes a rotation body and a sleeve. The rotation body includes a shaft, a first tube element, and a second tube element. The shaft is pivoted in the housing. The shaft has an annular protrusion, and the shaft is connected with the carrying module through the driving gear module. The first tube element is fixedly disposed in the housing and sleeved on the shaft, wherein the shaft is adapted to rotate relative to the first tube element. The second tube element is rotatably sleeved on the shaft and located between the first tube element and the annular protrusion. The sleeve is slidably disposed on the rotation body. The push rod is connected to the sleeve and aligned with any one of the slots. When the sleeve moves from a first position to a second position, the second tube element is propelled by the annular protrusion to rotate a first angle along a rotating direction relative to the first tube element, and the push rod is moved into the slot aligned with the push rod. When the sleeve moves from the second position to the first position, the second tube element is propelled by the sleeve to rotate the first angle along an opposite direction of the rotating direction relative to the first tube element, and the annular protrusion is respectively driven by the second tube element and the sleeve so that the shaft rotate a second angle relative to the first tube element, and the carrying module is driven by the driving gear module to rotate together so that the push rod is aligned with a next one of the slots.

A test device in the invention includes a housing, a carrying module, a driving gear module, a rotation body, and a sleeve. The carrying module is pivoted on the housing. The carrying module is used for carrying a plurality consumable elements. The rotation body includes a shaft, a first tube element, and a second tube element. The shaft is pivoted in the housing, wherein the shaft has an annular protrusion, and the shaft is connected with the carrying module through the driving gear module. The first tube element is fixedly disposed in the housing and sleeved on the shaft, wherein the shaft is adapted to rotate relative to the first tube element. The second tube element is rotatably sleeved on the shaft and located between the first tube element and the annular protrusion, wherein corresponding engaging portions engageable with each other are respectively disposed between the second tube element and the annular protrusion, and between the second tube element and the first tube element. The sleeve is slidably disposed on the rotation body. When the sleeve moves back and forth along a direction, the annular protrusion, the first tube element, and the second tube element are adapted to switch between an engaged state and a non-engaged state, so as to make the second tube element rotate back and forth, and to drive the annular protrusion and the shaft to rotate along a rotating direction, thereby driving the carrying module to rotate.

According to an embodiment of the invention, a periphery surface of the annular protrusion has a plurality of first protrusions, a peripheral surface of the first tube element has a slide track, a peripheral surface of the second tube element has a second protrusion, and the sleeve has a slide groove disposed correspond to the slide track. The annular protrusion, the first tube element, and the second tube element are adapted to switch between an engaged state and a non-engaged state.

According to an embodiment of the invention, the annular protrusion further has a first engaging portion, the first tube element has a second engaging portion, and the second tube element has a third engaging portion and a fourth engaging portion opposite to each other. The third engaging portion corresponds to the first engaging portion, and the fourth engaging portion corresponds to the second engaging portion. In the engaged state, the first engaging portion and the third engaging portion are engaged with each other, and the second engaging portion and the fourth engaging portion are engaged with each other. In the non-engaged state, the first engaging portion and the third engaging portion are not engaged with each other, and the second engaging portion and the fourth engaging portion are not engaged with each other.

According to an embodiment of the invention, when the sleeve is located at the first position, the annular protrusion, the first tube element, and the second tube element are in the non-engaged state, and the first protrusions and the second protrusion are aligned with the slide groove. When the sleeve is located at the second position, the annular protrusion, the first tube element, the second tube element are in the engaged state, the first protrusions are aligned with the slide groove, and the second protrusion are not aligned with the slide groove.

According to an embodiment of the invention, an opening of the slide groove has a guiding slanted surface. When the sleeve returns from the second position to the first position, the guiding slanted surface sequentially interferes with the second protrusion and the first protrusions, and the guiding slanted surface sequentially guides the second protrusion and the first protrusions into the slide groove.

According to an embodiment of the invention, when the sleeve moves from the second position to the first position further includes a transition position located between the second position and the first position. When the sleeve is located at the transition position, the annular protrusion and the second tube element are engaged with each other, the first tube element and the second tube element are not engaged with each other, the second protrusion is located in the slide groove, and the first protrusions are not aligned with the slide groove.

According to an embodiment of the invention, when the sleeve moves from the transition position to the first position, the annular protrusion is driven by the sleeve so that the shaft rotates a third angle along the opposite direction of the rotating direction, wherein the second angle is equaled to a sum of the third angle and the first angle.

In summary, in the rotation module according to embodiments of the invention, due to back and forth movement of the sleeve between the first position and the second position, the sleeve may drive the second tube element sleeved on the shaft to rotate a first angle along a rotating direction and along an opposite direction of the rotating direction. During the operational process, the shaft may be respectively driven by the second tube element and the sleeve to rotate a second angle along the opposite direction of the rotating direction. In specifics, when the sleeve is located at the first position, the push rod is aligned with any one of the slots on the carrying cartridge, in which consumable elements are slidably disposed in the slot. When the sleeve moves from the first position to the second position, the push rod passes through the slot and pushes the consumable elements in the slot out of the carrying cartridge, and accordingly the user can perform the related test operations.

On the other hand, the carrying module and the shaft are connected through the driving gear module. Therefore, when the shaft rotates the second angle along the opposite direction of the rotating direction, the shaft may simultaneously drive the carrying module to rotate relative to the housing, such that the push rod is aligned with the next slot. In other words, the rotation module in the invention can increase the rotational accuracy to the assigned locations. Accordingly, the test device applying the rotation module can achieve automatic replacement of consumable elements by having the rotation module drive the rotation of the carrying module, and thereby enhance the user convenience during operation.

Several exemplary embodiments accompanied with figures are described in detail below to further describe the invention in details.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF EMBODIMENTS

Figure 1:
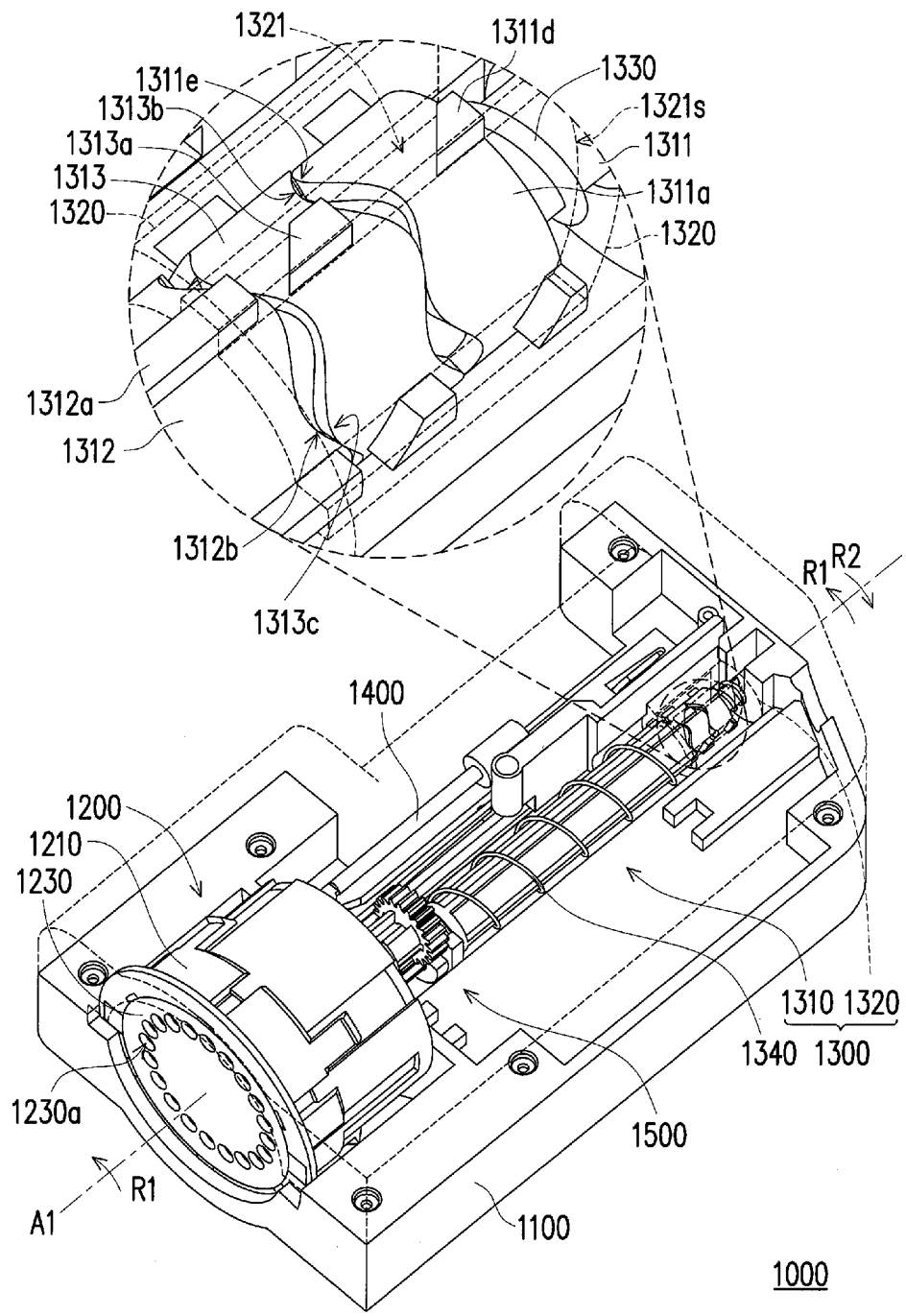
FIG. 1 to FIG. 5 are schematic views illustrating an operation of a test device and a rotation module thereof according to an embodiment of the invention.
Figure 2:
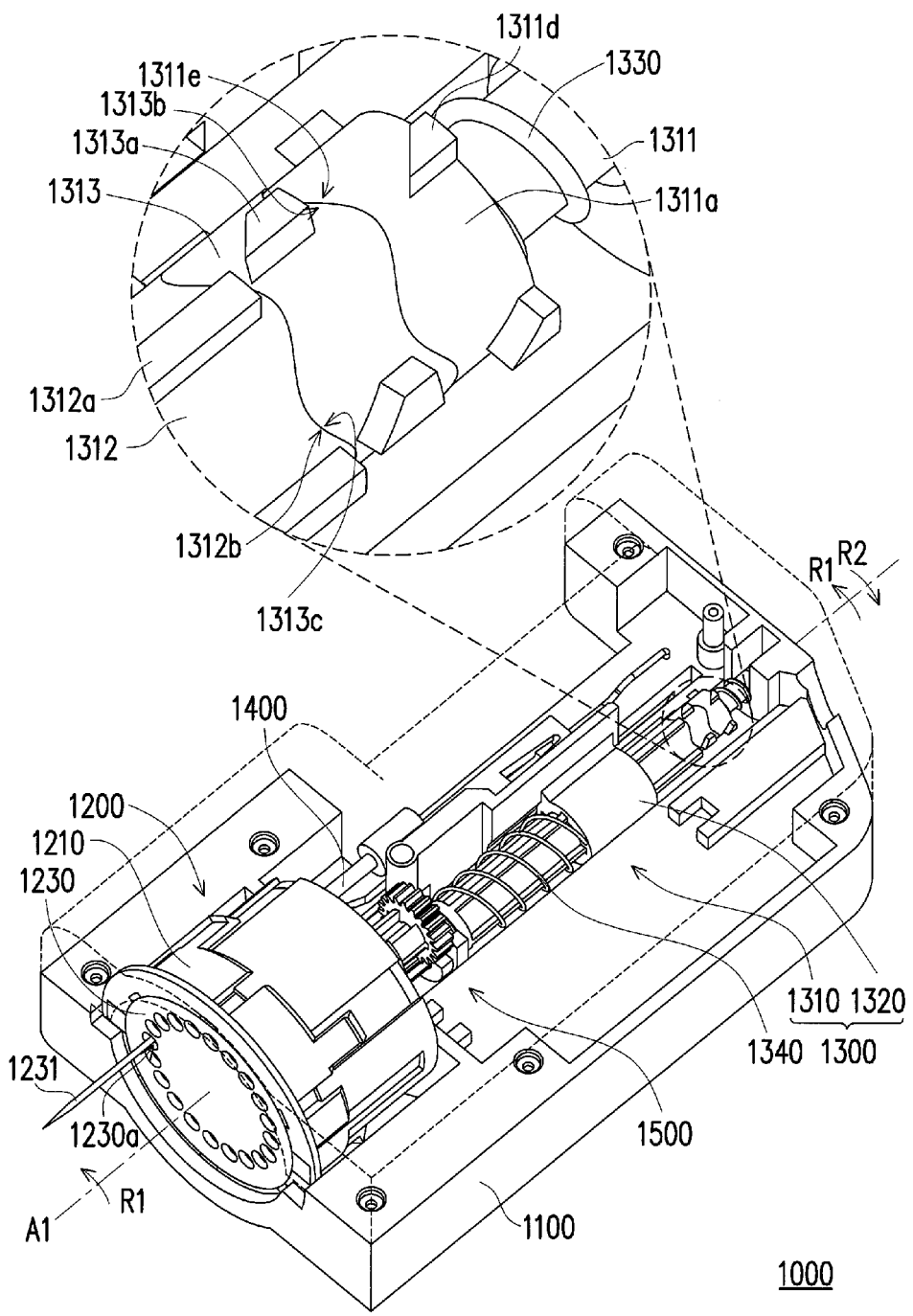

FIG. 1 to FIG. 5 are schematic views illustrating an operation of a test device and a rotation module thereof according to an embodiment of the invention. With reference to FIG. 1 and FIG. 2, in the present embodiment, a test device 1000 includes a housing 1100, a carrying module 1200, a rotation module 1300, a push rod 1400, and a driving gear module 1500. The housing 1100 may be formed by plastic, acrylic, metal, carbon fiber, composite materials, or other suitable materials.

The carrying module 1200 may be pivoted on the housing 1100 along a first axial line A1, and the carrying module 1200 may be connected with the rotation module 1300 through the driving gear module 1500. The carrying module 1200 may be driven to rotate by each rotation of the rotation module 1300 through the driving gear module 1500. In specifics, the carrying module 1200 may include a carrier 1210 and a carrying cartridge 1230 detachably disposed on the carrier 1210. The carrier 1210 is connected to the driving gear module 1500, and the carrier 1210 is driven to rotate by each rotation of the rotation module 1300 through the driving gear module 1500, while the carrier 1210 simultaneously drives the carrying cartridge 1230 disposed on the carrier 1210 to rotate.

On the other hand, the carrying cartridge 1230 has a plurality of slots 1230a and a plurality of consumable elements 1231 slidably disposed in the slots 1230a. The push rod 1400 may correspond to any one of the slots 1230a in the plurality of slots 1230a. Moreover, each rotation of the rotation module 1300 may drive the carrying cartridge 1230a to perform a rotation process, and each rotation process may make the push rod 1400 correspond to a next one of the slots 1230a. In other words, due to each rotation of the rotation module 1300, the push rod 1400 may sequentially correspond to each of the slots 1230a. In addition, the push rod 1400 may sequentially pass through each of the corresponding slots 1230a in order to send the consumable elements 1231 slidably disposed in each of the slots 1230a out of the carrying cartridge 1230. In the drawings, the consumable elements 1231 are shown as blood lancets as an illustrative example, although the invention is not limited thereto. In other embodiments, the consumable elements 1231 may also be test strips.

The rotation module 1300 is disposed in the housing 1100, and the rotation module 1300 includes a rotation body 1310 and a sleeve 1320. The rotation body 1310 includes a shaft 1311, a first tube element 1312, and a second tube element 1313. The shaft 1311 is connected to the carrying module 1200 through the driving gear module 1500. In specifics, each rotation of the shaft 1311, the shaft 1311 may drive the carrying module 1200 to rotate through the driving gear module 1500. In the present embodiment, the first tube element 1312 and the second tube element 1313 are respectively sleeved on the shaft 1311, wherein the second tube element 1313 may be rotatably sleeved on the shaft 1311, and the first tube element 1312 is fixedly disposed in the housing 1100. In other words, the shaft 1311 may be rotatably disposed in the first tube element 1312. Moreover, the shaft 1311 has an annular protrusion 1311a, and the second tube element 1313 is located between the first tube element 1312 and the annular protrusion 1311a. In the present embodiment, the annular protrusion 1311a on the shaft 1311 has a plurality of first protrusions 1311d, and the first protrusions 1311d are spaced equally on a peripheral surface of the annular protrusion 1311a. In addition, a peripheral surface of the first tube element 1312 has a slide track 1312a, and a peripheral surface of the second tube element 1313 has a second protrusion 1313a.

With reference to FIG. 1 and FIG. 2, the annular protrusion 1311a on the shaft 1311 further has a first engaging portion 1311e, and the first tube element 1312 has a second engaging portion 1312b. Moreover, the second tube element 1313 has a third engaging portion 1313b and a fourth engaging portion 1313c opposing each other, and the third engaging portion 1313b and the fourth engaging portion 1313c respectively correspond to the first engaging portion 1313e and the second engaging portion 1313b. In specifics, the first engaging portion 1313e and the third engaging portion 1313b may be tooth pattern structures or wave pattern structures with complementary profiles, and the second engaging portion 1312b and the fourth engaging portion 1313c may be tooth pattern structures or wave pattern structures with complementary profiles. Between the annular protrusion 1311a, the first tube element 1312, and the second tube element 1313, there may be an engaged state and a non-engaged state, and the three elements are adapted to convert between the engaged state and the non-engaged state. In the engaged state, the first engaging portion 1311e engages with the third engaging portion 1313b, and the second engaging portion 1312b engages with the fourth engaging portion 1313c, as shown in FIG. 2. In the non-engaged state, the first engaging portion 1311e does not engage with the third engaging portion 1313b, and the second engaging portion 1312b does not engage with the fourth engaging portion 1313c, as shown in FIG. 1. Moreover, in the present embodiment, a prestressing force is applied between the annular protrusion 1311a, the first tube element 1312, and the second tube element 1313 so the elements remain in the engaged state.

In the present embodiment, the sleeve 1320 is slidably disposed on the rotation body 1310, and the sleeve 1320 is adapted to move back and forth between a first position and a second position. In specifics, the sleeve 1320 has a slide groove 1321 configured corresponding to the slide track 1312a, such that the sleeve 1320 can move back and forth between the first position and the second position along the slide track 1312a. As shown in FIG. 1, when the sleeve 1320 is located at the first position, the annular protrusion 1311a, the first tube element 1312, and the second tube element 1313 are in the non-engaged state, and the first protrusions 1311d and the second protrusion 1313a are aligned with the slide groove 1321. As shown in FIG. 2, when the sleeve 1320 is located at the second position, the annular protrusion 1311a, the first tube element 1312, and the second tube element 1313 are in the engaged state, and the first protrusions 1311d are aligned with the slide groove 1321, whereas the second protrusion 1313a is not aligned with the slide groove 1321.

In the present embodiment, a reciprocal motion performed by the sleeve 1320 between the first position and the second position corresponds to a stroke of the push rod 1400, which is the motion of the push rod 1400 pushing the consumable elements 1231 out and returning to position, as depicted in the operation flow shown in FIG. 1 to FIG. 5. In the present embodiment, the sleeve 1320 and the push rod 1400 may be connected to each other, such that when either one of the sleeve 1320 or the push rod 1400 is pushed, the other element can move correspondingly. Moreover, in the present embodiment, each reciprocal motion of the sleeve 1320 drives the rotation module 1300 to rotate once, thereby making the carrying cartridge 1230 perform a rotation process. At the same time of the aforementioned process, the push rod 1400 completes a stroke to push out the consumable elements 1231 in the corresponding slot 1230a, and the push rod 1400 corresponds to the next slot 1230a after returning to position.

The operational flow and the corresponding relationships between each of the elements in the present embodiment are further described hereafter.

With reference to FIG. 1, the figure depicts an initial state of the test device 1000, which is the state before operation begins. In the initial state, the sleeve 1320 is located at the first position, and the first protrusions 1311d and the second protrusion 1313a are located in the slide groove 1321 and aligned with the slide groove 1321. Moreover, the first protrusions 1311d and the second protrusion 1313a are restricted by the slide groove 1321 so as to resist the prestressing force, such that the annular protrusion 1311a, the first tube element 1312, and the second tube element 1313 are in the non-engaged state. With reference to FIG. 2, when the sleeve 1320 moves from the first position to the second position, the first protrusions 1311d and the second protrusion 1313a are released from the slide groove 1321. Due to motion from the prestressing force, the second tube element 1313 is propelled by the annular protrusion to rotate a first angle along a rotating direction R1 relative to the first tube element 1312, such that the annular protrusion 1311a, the first tube element 1312, and the second tube element 1313 are in the engaged state. Since the second tube element 1313 rotates the first angle relative to the first tube element 1312, therefore, in the engaged state, the second protrusion 1313a is not aligned with the slide groove 1321. In addition, when the sleeve 1320 moves from the first position to the second position, since the shaft 1311 does not rotate relative to the first tube element 1312, therefore, in the engaged state, the first protrusions 1311d are still aligned with the slide groove 1321. When the sleeve 1320 moves from the first position to the second position, the push rod 1400 moves into the corresponding slot 1230a, so as to push the consumable elements 1231 in the slot 1230a out of the carrying cartridge 1230.

In the present embodiment, the rotation module 1300 further includes a first elastic element 1330 and a second elastic element 1340. The first elastic element 1330 is sleeved on the shaft 1311 and abutted between the annular protrusion 1311a and the housing 1100. The first elastic element 1330 provides the prestressing force which maintains the annular protrusion 1311a, the first tube element 1312, and the second tube element 1313 are in the engaged state. On the other hand, the second elastic element 1340 is sleeved on the first tube element 1312 and abutted on the sleeve 1320. The second elastic element 1340 provides a restoring force to make the sleeve 1320 return from the second position to the first position. When the sleeve 1320 is located at the first position, due to restriction by the slide groove 1321, the annular protrusion 1311a, the first tube element 1312, and the second tube element 1313 are in the non-engaged state, and the first elastic element 1330 is compressed. Therefore, when the sleeve 1320 moves from the first position to the second position, the elastic restoring force of the first elastic element 1330 may drive the annular protrusion 1311a and make the third engaging portion 1313b move relative to the first engaging portion 1311e to engage with each other. At the same time, the fourth engaging portion 1313c moves relative to the second engaging portion 1312b to engage with each other.

Figure 3:
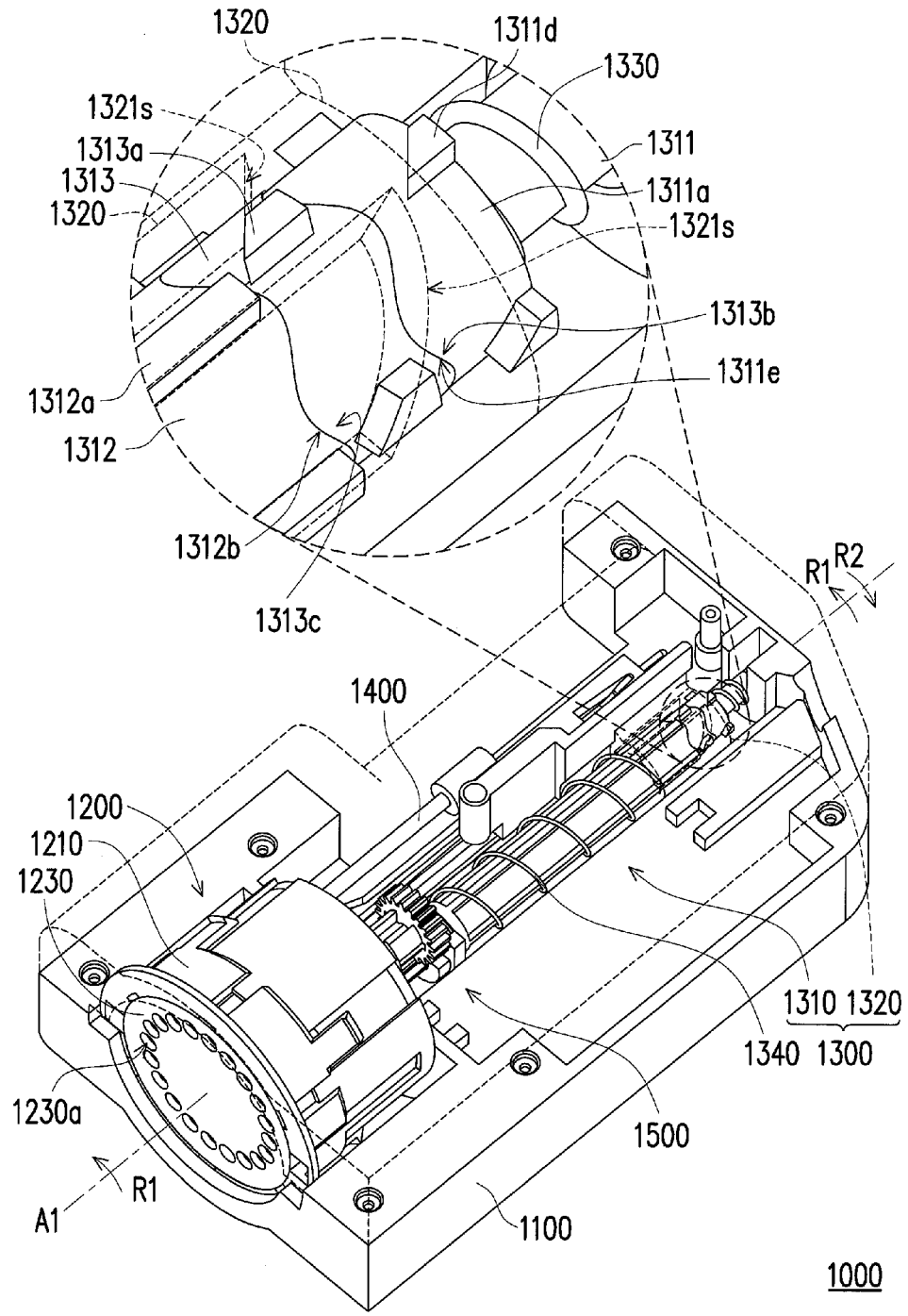
Figure 4:
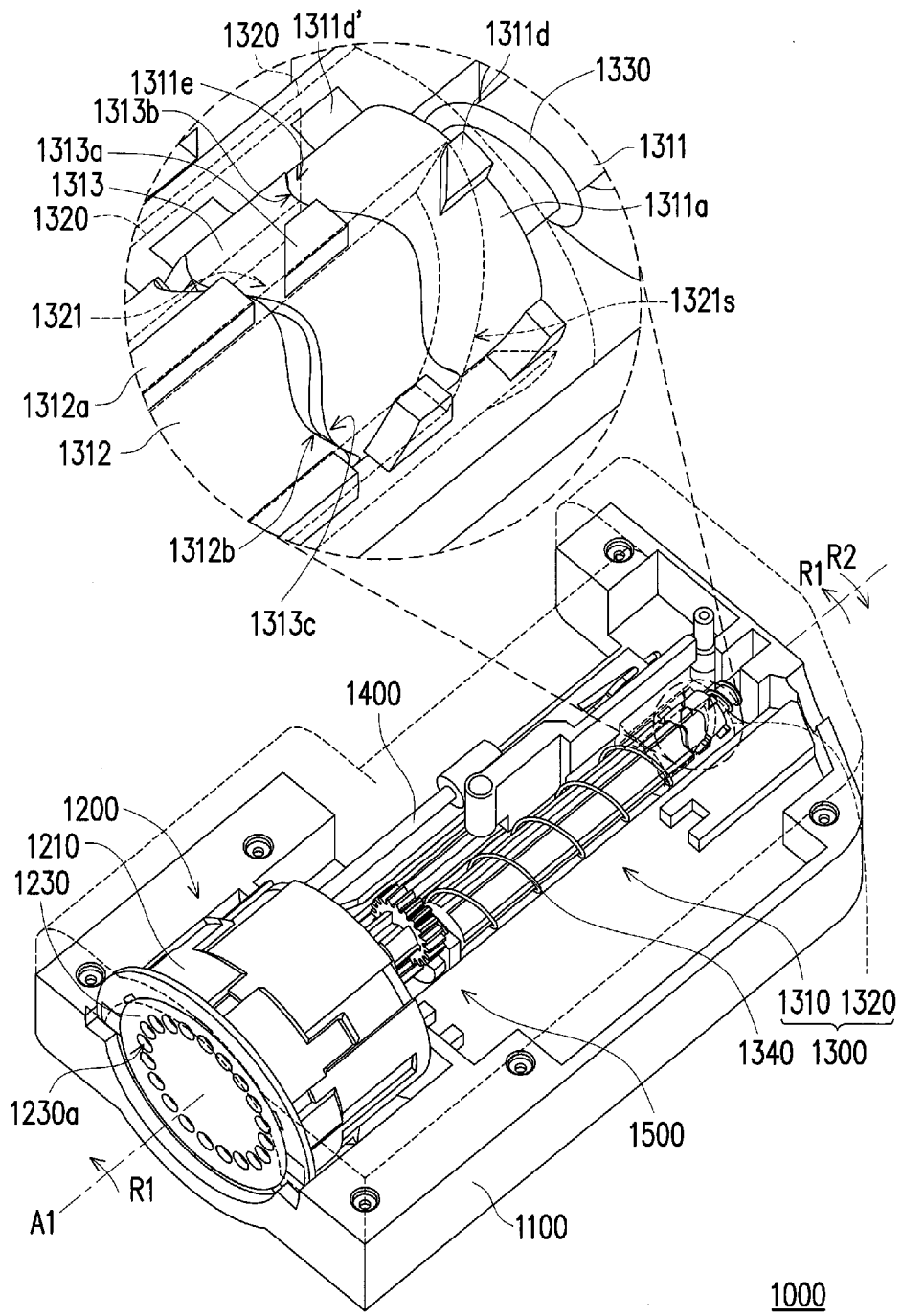
Figure 5:
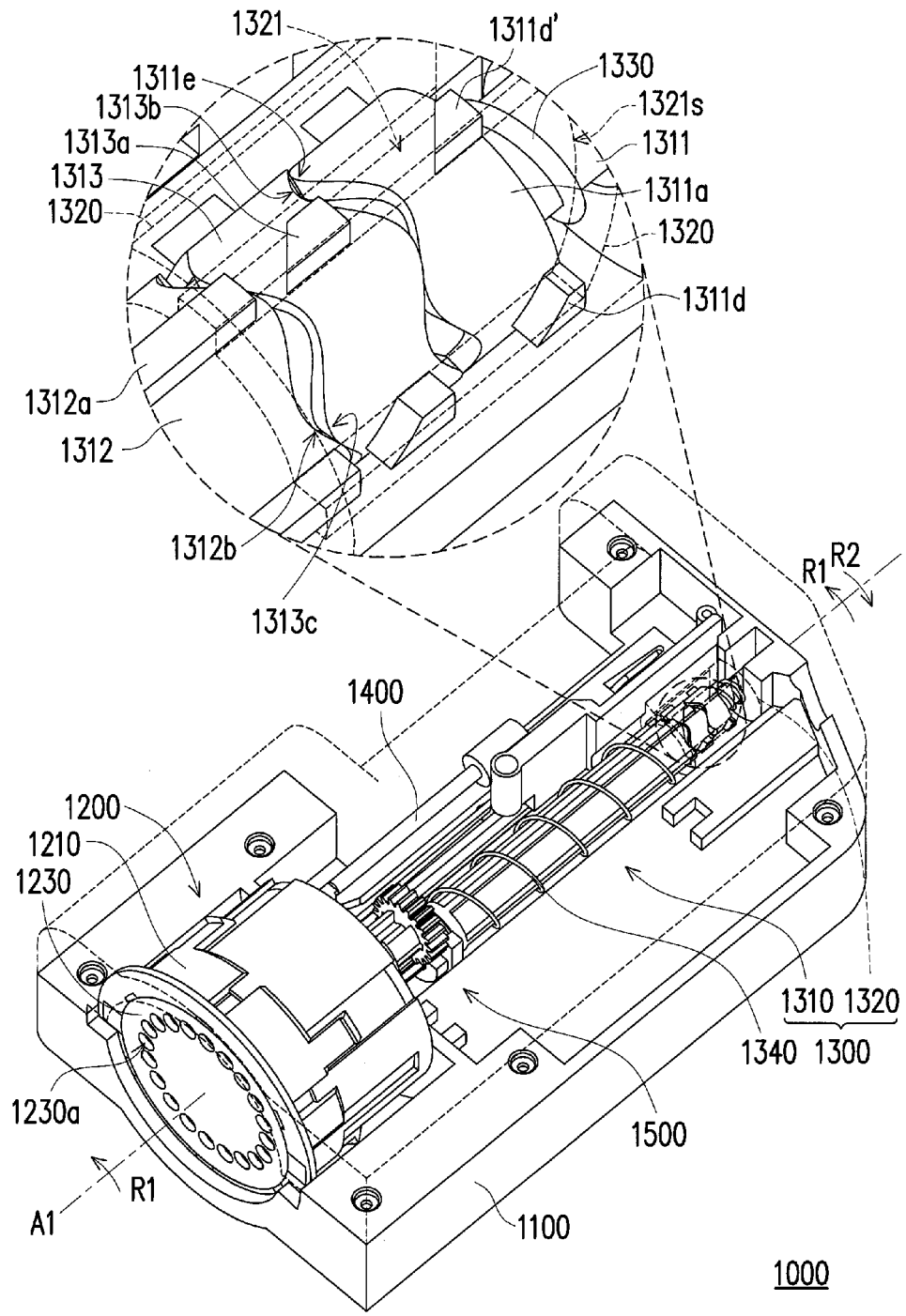

Furthermore, when the sleeve 1320 moves from the first position to the second position, the second elastic element 1340 is propelled by the sleeve 1320 and becomes compressed. Therefore, when the external force driving the sleeve 1320 or the push rod 1400 is removed, an elastic restoring force of the second elastic element 1340 may drive the sleeve 1320 to move toward the first position. With reference to FIG. 3 to FIG. 5, these drawings depict the operational flow of the sleeve 1320 moving from the second position to the first position and the corresponding relationships between each of the elements according to an embodiment of the invention. In the present embodiment, an opening of the slide groove 1321 has a guiding slanted surface 1321s. When the sleeve 1320 returns from the second position to the first position, the guiding slanted surface 1321s sequentially interferes with the second protrusion 1313a and the first protrusions 1311d, and the guiding slanted surface 1321s sequentially guides the second protrusion 1313a and the first protrusions 1311d into the slide groove 1321.

With reference to FIG. 2 and FIG. 3, when the sleeve 1320 is located at the second position, the annular protrusion 1311a, the first tube element 1312, and the second tube element 1313 are in the engaged state, the first protrusions 1311d is aligned with the slide groove 1321, and the second protrusion 1313a is not aligned with the slide groove 132, as shown in FIG. 2. Therefore, when of the slide groove 1321 of the sleeve 1320 returns from the second position to the first position along the slide track 1312a of the first tube element 1312, the second protrusion 1313a which is not aligned with the slide groove 1321 would first interfere with the guiding slanted surface 1321s located at the opening of the slide groove 1321, as shown in FIG. 3. When the sleeve 1320 continues to move toward the first position, the guiding slanted surface 1321s may guide the second protrusion 1313a into the slide groove 1321, as shown in FIG. 4.

According to the present embodiment, when the sleeve 1320 moves from the second position to the first position further includes a transition position located between the second position and the first position, as shown in FIG. 4. When the sleeve 1320 is located at the transition position, the annular protrusion 1311a and the second tube element 1313 are in the engaged state, and the first tube element 1312 and the second tube element 1313 are in the non-engaged state.

Moreover, the second protrusion 1313a is located in the slide groove 1321, so that the first protrusions 1311d are not aligned with the slide groove 1321.

Furthermore, when the second tube element 1313 is propelled by the guiding slanted surface 1321s, the second tube element 1313 may rotate the first angle along a second rotating direction R2 (e.g., opposite direction of the first rotating direction R1) relative to the first tube element 1312, such that the fourth engaging portion 1313c moves relative to the second engaging portion 1312b and returns to the non-engaged state, whereas the first engaging portion 1311e and the third engaging portion 1313b are still engaged with each other. At this time, since the first engaging portion 1311e and the third engaging portion 1313b are still engaged with each other, therefore, when the second tube element 1313 rotates the first angle along the second rotating direction R2 relative to the first tube element 1312, the second tube element 1313 can simultaneously drive the shaft 1311 to rotate the first angle along the second rotating direction R2, so that the first protrusions 1311d are not aligned with the slide groove 1321. Based on the foregoing description, when the sleeve 1320 moves back and forth between the first position and the second position, the second tube element 1313 may rotate back and forth within a range of the first angle.

On the other hand, at the same time when the shaft 1311 rotates the first angle along the second rotating direction R2, the driving gear module 1500 may also drive the carrying module 1200 to rotate together. Moreover, as shown in FIG. 4, when the sleeve 1320 is located at the transition position, under the driving of the second tube element 1313, besides the first protrusions 1311d being rotated the first angle to be not aligned with the slide groove 1321, a next first protrusion 1311d' after rotation interferes with the guiding slanted surface 1321s located at the opening of the slide groove 1321. Thereafter, as shown in FIG. 5, when the sleeve 1320 moves from the transition position to the first position, the guiding slanted surface 1321s guides the next first protrusion 1311d' into the slide groove 1321, such that the first engaging portion 1311e moves relative to the third engaging portion 1313b and returns to the non-engaged state. When the guiding slanted surface 1321s guides the next protrusion 1311d' into the slide groove 1321, the shaft 1311 continues to rotate a third angle along the second rotating direction R2. At this time, the first protrusions 1311d and the second protrusion 1313a are located in the slide groove 1321 again, and the annular protrusion 1311a, the first tube element 1312, and the second tube element 1313 are again in the non-engaged state, and thus completing one rotation of the rotation module 1300.

In other words, by respectively driving the annular protrusion 1311a with the second tube element 1313 and the sleeve 1320, the shaft 1311 can rotate a second angle along the second rotating direction R2 relative to the first tube element 1312, wherein the second angle may be equaled to a sum of the first angle and the third angle, and thereby complete one rotation of the rotation module 1300. On the other hand, while the shaft 1311 is rotating, the driving gear module 1500 may drive the carrying module 1200 to perform a rotation process relative to the housing 1100, so that the push rod 1400 moved back to the initial position is aligned with the next slot 1230a.

That is, while the push rod 1400 pushes the consumable elements 1231 out of the carrying cartridge 1230, the sleeve 1320 also moves from the first position to the second position. During this process, the shaft 1311 does not rotate, and correspondingly, the carrying module 1200 also does not rotate. Thereafter, while the push rod 1400 returns to the initial position, the sleeve 1320 also returns from the second position to the first position. During this process, the shaft 1311 is respectively driven by the second tube element 1313 and the sleeve 1320 to rotate. Moreover, the carrying module 1200 is driven by the driving gear module 1500 to perform a rotation process, so as to accurately rotate a next slot 1230a into a fixed position. Accordingly, the push rod 1400 moved back to the initial location is aligned with the next slot 1230a, thereby achieving automatic replacement of consumable elements 1231 in the carrying module 1200, so as to prevent repeated use of the consumable elements 1231. Furthermore, since the carrying cartridge 1230 can be detachably disposed on the carrier 1210, therefore, after the consumable elements 1231 in the carrying cartridge 1230 have been used up, the user may remove the old carrying cartridge 1230 from the carrier 1210 and continue usage by replacing it with a new carrying cartridge 1230.

In an embodiment of the invention, the rotation module may be implemented by a slide track, a slide groove, a second protrusion, and in combination with a plurality of first protrusions. When the sleeve passes through the slide groove and moves back and forth between the first position and the second position along the slide track, the sleeve may drive the second protrusion to rotate back and forth, and also drive the first protrusions to rotate in order to sequentially guide the next first protrusion into the slot. In another embodiment of the invention, the rotation module may be implemented by a slide track, a second protrusion, a first protrusion, and in combination with a plurality of slide grooves. When the sleeve passes through any one of the slide grooves and moves back and forth between the first position and the second position along the slide track, the sleeve may drive the second protrusion to rotate back and forth, and also drive the first protrusion to rotate in order to sequentially guide the first protrusion to the next slide groove. In another embodiment of the invention, in order for the rotation module to rotate stably, the rotation module may be implemented by a plurality of sets of corresponding slide tracks, second protrusions, first protrusions, and first protrusions.

In summary, in the rotation module according to embodiments of the invention, due to back and forth movement of the sleeve between the first position and the second position, the sleeve may drive the second tube element sleeved on the shaft to rotate a first angle along a rotating direction and along an opposite direction of the rotating direction. During the operational process, the shaft may be respectively driven by the second tube element and the sleeve to rotate a second angle along the opposite direction of the rotating direction. In specifics, when the sleeve is located at the first position, the push rod is aligned with any one of the slots on the carrying cartridge, in which consumable elements are slidably disposed in the slot. When the sleeve moves from the first position to the second position, the push rod passes through the slot and pushes the consumable elements in the slot out of the carrying cartridge, and accordingly the user can perform the related test operations.

On the other hand, the carrying module and the shaft are connected through the driving gear module. Therefore, when the shaft rotates the second angle along the opposite direction of the rotating direction, the shaft may also drive the carrying module to rotate relative to the housing, such that the push rod is aligned with the next slot. In other words, the rotation module in the invention can increase the rotational accuracy to the assigned locations. Accordingly, the test device applying the rotation module can achieve automatic replacement of consumable elements by having the rotation module drive the rotation of the carrying module, and thereby enhance the user convenience during operation.

It will be apparent to those skilled in the art that various modifications and variations can be made to the structure of the disclosed embodiments without departing from the scope or spirit of the invention. In view of the foregoing, it is intended that the disclosure cover modifications and variations of this specification provided they fall within the scope of the following claims and their equivalents.

What is claimed is:

1. A rotation module disposed in a housing of a test device, the rotation module comprising:
   a rotation body, comprising:
   a shaft pivoted in the housing, the shaft having an annular protrusion;
   a first tube element fixedly disposed in the housing and sleeved on the shaft, wherein the shaft is adapted to rotate relative to the first tube element; and
   a second tube element rotatably sleeved on the shaft and located between the first tube element and the annular protrusion; and
   a sleeve slidably disposed on the rotation body, when the sleeve moves from a first position to a second position, the second tube element is propelled by the annular protrusion to rotate a first angle along a rotating direction relative to the first tube element, when the sleeve moves from the second position to the first position, the second tube element is propelled by the annular protrusion to rotate the first angle along an opposite direction of the rotating direction relative to the first tube element, and the annular protrusion is respectively driven by the second tube element and the sleeve so that the shaft rotates a second angle relative to the first tube element.

2. The rotation module as recited in claim 1, wherein a periphery surface of the annular protrusion has a plurality of first protrusions, a peripheral surface of the first tube element has a slide track, a peripheral surface of the second tube element has a second protrusion, and the sleeve has a slide groove disposed correspond to the slide track, wherein the annular protrusion, the first tube element, and the second tube element are adapted to switch between an engaged state and a non-engaged state.

3. The rotation module as recited in claim 2, wherein the annular protrusion further has a first engaging portion, the first tube element has a second engaging portion, and the second tube element has a third engaging portion and a fourth engaging portion opposite to each other, the third engaging portion corresponding to the first engaging portion, the fourth engaging portion corresponding to the second engaging portion, wherein in the engaged state, the first engaging portion and the third engaging portion are engaged with each other, and the second engaging portion and the fourth engaging portion are engaged with each other, wherein in the non-engaged state, the first engaging portion and the third engaging portion are not engaged with each other, and the second engaging portion and the fourth engaging portion are not engaged with each other.

4. The rotation module as recited in claim 2, wherein when the sleeve is located at the first position, the annular protrusion, the first tube element, and the second tube element are in the non-engaged state, and the first protrusions and the second protrusion are aligned with the slide groove, and when the sleeve is located at the second position, the annular protrusion, the first tube element, the second tube element are in the engaged state, and the first protrusions are aligned with the slide groove, the second protrusion being not aligned with the slide groove.

5. The rotation module as recited in claim 2, wherein an opening of the slide groove has a guiding slanted surface, when the sleeve returns from the second position to the first position, the guiding slanted surface sequentially interferes with the second protrusion and the first protrusions, and the guiding slanted surface sequentially guides the second protrusion and the first protrusions into the slide groove.

6. The rotation module as recited in claim 2, wherein when the sleeve moves from the second position to the first position further comprises a transition position located between the second position and the first position, and when the sleeve is located at the transition position, the annular protrusion and the second tube element are engaged with each other, the first tube element and the second tube element are not engaged with each other, the second protrusion is located in the slide groove, and the first protrusions are not aligned with the slide groove.

7. The rotation module as recited in claim 6, wherein when the sleeve moves from the transition position to the first position, the annular protrusion is driven by the sleeve so that the shaft rotates a third angle along the opposite direction of the rotating direction, wherein the second angle is equaled to a sum of the third angle and the first angle.

8. A test device, comprising:
a housing;
a carrying module pivoted on the housing, the carrying module having a plurality of slots;
a driving gear module;
a rotation module disposed in the housing, the carrying module is connected with the rotation module through the driving gear module, the rotation module comprising:
a rotation body, comprising:
a shaft pivoted in the housing, the shaft having an annular protrusion, and the shaft is connected with the carrying module through the driving gear module;
a first tube element fixedly disposed in the housing and sleeved on the shaft,
wherein the shaft is adapted to rotate relative to the first tube element; and
a second tube element rotatably sleeved on the shaft and located between the first tube element and the annular protrusion; and
a sleeve slidably disposed on the rotation body; and
a push rod connected to the sleeve and aligned with any one of the slots,
wherein, when the sleeve moves from a first position to a second position, the second tube element is propelled by the annular protrusion to rotate a first angle along a rotating direction relative to the first tube element, and the push rod is moved into the slot aligned with the push rod, when the sleeve moves from the second position to the first position, the second tube element is propelled by the sleeve to rotate the first angle along an opposite direction of the rotating direction relative to the first tube element, and the annular protrusion is respectively driven by the second tube element and the sleeve so that the shaft rotates a second angle relative to the first tube element, and the carrying module is driven by the driving gear module to rotate so that the push rod is aligned with a next one of the slots.

9. The test device as recited in claim 8, wherein a periphery surface of the annular protrusion has a plurality of first protrusions, a peripheral surface of the first tube element has a slide track, a peripheral surface of the second tube element has a second protrusion, and the sleeve has a slide groove disposed correspond to the slide track, wherein the annular protrusion, the first tube element, and the second tube element are adapted to switch between an engaged state and a non-engaged state.

10. The test device as recited in claim 9, wherein the annular protrusion further has a first engaging portion, the first tube element has a second engaging portion, and the second tube element has a third engaging portion and a fourth engaging portion opposite to each other, the third engaging portion corresponding to the first engaging portion, the fourth engaging portion corresponding to the second engaging portion, wherein in the engaged state, the first engaging portion and the third engaging portion are engaged with each other, and the second engaging portion and the fourth engaging portion are engaged with each other, wherein in the non-engaged state, the first engaging portion and the third engaging portion are not engaged with each other, and the second engaging portion and the fourth engaging portion are not engaged with each other.

11. The test device as recited in claim 9, wherein when the sleeve is located at the first position, the annular protrusion, the first tube element, and the second tube element are in the non-engaged state, and the first protrusions and the second protrusion are aligned with the slide groove, and when the sleeve is located at the second position, the annular protrusion, the first tube element, and the second tube element are in the engaged state, and the first protrusions are aligned with the slide groove, the second protrusion being not aligned with the slide groove.

12. The test device as recited in claim 9, wherein an opening of the slide groove has a guiding slanted surface, and when the sleeve returns from the second position to the first position, the guiding slanted surface sequentially interferes with the second protrusion and the first protrusions, and the guiding slanted surface sequentially guides the second protrusion and the first protrusions into the slide groove.

13. The test device as recited in claim 9, wherein when the sleeve moves from the second position to the first position further comprises a transition position located between the second position and the first position, and when the sleeve is located at the transition position, the annular protrusion and the second tube element are engaged with each other, the first tube element and the second tube element are not engaged with each other, the second protrusion is located in the slide groove, and the first protrusions are not aligned with the slide groove.

14. The test device as recited in claim 13, wherein when the sleeve moves from the transition position to the first position, the annular protrusion is driven by the sleeve so that the shaft rotates a third angle along the opposite direction of the rotating direction, wherein the second angle is equaled to a sum of the third angle and the first angle.

15. A test device, comprising:
a housing;
a carrying module pivoted on the housing, the carrying module used for carrying a plurality consumable elements;
a driving gear module;
a rotation body, comprising:
a shaft pivoted in the housing, the shaft having an annular protrusion, and the shaft is connected with the carrying module through the driving gear module;
a first tube element fixedly disposed in the housing and sleeved on the shaft, wherein the shaft is adapted to rotate relative to the first tube element; and
a second tube element rotatably sleeved on the shaft and located between the first tube element and the annular protrusion, wherein corresponding engaging portions engageable with each other are respectively disposed between the second tube element and the annular protrusion, and between the second tube element and the first tube element; and a sleeve slidably disposed on the rotation body;

wherein, when the sleeve moves back and forth along a direction, the annular protrusion, the first tube element, and the second tube element are adapted to switch between an engaged state and a non-engaged state, so as to make the second tube element rotate back and forth, and to drive the annular protrusion and the shaft to rotate along a rotating direction, thereby driving the carrying module to rotate.

\* \* \* \* \*